(12) United States Patent
Lal et al.

(10) Patent No.: US 7,030,283 B2
(45) Date of Patent: Apr. 18, 2006

(54) PROCESS FOR PRODUCING 1,1-DIFLUOROVINYL CYCLOALIPHATIC COMPOUNDS

(75) Inventors: Gauri Sankar Lal, Whitehall, PA (US); Kathryn Sue Hayes, Plymouth Meeting, PA (US); Guido Peter Pez, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 143 days.

(21) Appl. No.: 10/763,366

(22) Filed: Jan. 23, 2004

(65) Prior Publication Data

US 2005/0165260 A1 Jul. 28, 2005

(51) Int. Cl.
*C07C 17/25* (2006.01)
*C07C 17/23* (2006.01)

(52) U.S. Cl. .................. 570/157; 570/140; 570/141; 570/142; 570/153; 570/155; 570/156

(58) Field of Classification Search ................ 570/157, 570/153, 155, 156, 140, 141, 142
See application file for complete search history.

(56) References Cited

U.S. PATENT DOCUMENTS

| 4,839,390 A | 6/1989 | Naumann et al. |
| 4,968,851 A | 11/1990 | Naumann et al. |
| 4,997,855 A | 3/1991 | Peake |
| 6,605,747 B1 | 8/2003 | Kondo et al. |
| 2002/0120168 A1 | 8/2002 | Kondo et al. |

FOREIGN PATENT DOCUMENTS

EP  0 688 752 B1  1/1999

OTHER PUBLICATIONS

W.R. Moore, et al, Terminal Difluoro Olefin Analogues of Squalene Are.., J. Am. Chem. Soc., 1992, 114, p. 360-361.
W.R. Hertler, Substituted Quinodimethans, J. Am. Chem. Soc., 1963, p. 2877-2879.
Michio Obayashi, et al, (Diethylphosphinyl) Difluoromethyllithium, Tett. Letters, 1982, vol. 23, p. 2323-2326.
D.P. Matthews, et al, A New Method for The Electrophilic Fluorination of Vinly Stannanes, Tett. Letters, 1993, vol. 34, No. 19, p. 3057-3060.
Kyung-II Kim, et al, A New Route to 1,1-Difluoroelefins From Carboxylic Acids, Tett. Letters, 1996, vol. 37, No. 19, p. 3223-3226.
Takashi Okano, et al, Addition-Elimination Reaction of Highly Electrophilic .., Heterocyclic Communications, 1999, vol. 5, No. 2, p. 163-166.
Julian Legros, Trifluoromethylcyclohexane As A New Solvent?, Tetrahedron 58, 2002, p. 4067-4070.
L. Lochmann, et al, Interactions of Alkoxides, J. of Organometallic Chem., 1979, 179, p. 124-132.
P-H Liang, et al; Bioorg. Med. Chem., vol. 10, No. 10, 2002, pp. 3267-3276. Abstract.
T. Balko, et al; Tetrahedron Lett.; 40; 35; 1999; pp. 6347-6352. Abstract.
R. Sarnell, et al; Tetrahedron, 36; 1980; pp. 3241-3248. Abstract.
D. Naae, et al; Synth. Commun., 3; 1973; pp. 197-200. Abstract.
G.A. Wheaton, et al; Tetrahedron Lett., 1976, pp. 895-898. Abstract.

*Primary Examiner*—Elvis O. Price
(74) *Attorney, Agent, or Firm*—Geoffrey L. Chase

(57) ABSTRACT

This invention relates to a process for the preparation of 1,1-difluoroolefins, e.g., difluorovinyl cycloaliphatic compounds such as difluorovinylcyclohexane and derivatives by the dehydrofluorination of a trifluoromethyl-substituted cycloaliphatic compound and the resulting compositions. This method utilizes a "sterically hindered super-base" system represented by the formula $M^{+-}NRR^-$; where M is Na or K and R is a secondary, or tertiary alkyl or cycloalkyl group of amines for effecting dehydrofluorination of the trifluoromethyl group leading to the difluorovinyl based cycloaliphatic compounds. The sterically hindered super base can be formed by the, in situ, reaction of a sodium or potassium alkoxide, e.g., KtBuO with a lithium dialkylamide where the lithium is bonded to nitrogen atom of an amine bearing secondary or tertiary aliphatic groups.

17 Claims, No Drawings

PROCESS FOR PRODUCING 1,1-DIFLUOROVINYL CYCLOALIPHATIC COMPOUNDS

BACKGROUND OF THE INVENTION 1,1-Difluoroolefins are compounds that have attracted a great deal of attention because of their ability to react with various organic molecules. For example, these compounds have found application in designing diverse biological systems where they function as a mechanism-based enzyme inhibitor. They have been found to exhibit biocidal activity and can be used against pests that affect plants and animals. They have also been found to be a bioisostere of aldehydes and ketones. In addition, difluorovinyl cycloaliphatic compounds have been used as intermediates to difluoromethyl ethers for use as liquid crystal displays and as monomers for fluoroquinodimethane polymers.

The following articles and patents are representative of methods for forming 1,1-difluoroalkenes. They include:

Kyung Il Kim, et al, *A New Route to 1,1-Difluoroolefins From Carboxylic Acids*, Tetrahedron Letters, Vol. 19, 3223–3226 (1996) disclose methods for the synthesis of 1,1-difluoroolefins suitable for the design of biologically active molecules. Disclosed as the most versatile method for producing 1,1-difluoroolefins is the Wittig olefin synthesis. In this process an aldehyde is reacted with a phosphine, e.g., triphenylphosphine and sodium chlorodifluoroacetate. In their new route, carboxylic acids are converted first to dithioesters in a one-pot procedure. Then, $HgF_2$ is reacted with the dithioesters in the presence of HF-pyridine and KF to produce difluorothioethers which are oxidized to the corresponding sulfoxides and heated to produce the 1,1-difluoroolefins.

Matthews, D. P., et al, *A New Method For The Electrophilic Fluorination of Vinyl Stannanes*, Tetrahedron Letters, Vol. 34, No. 19, pp 3057–3060, 1993 disclose the use of vinyl stannanes for producing terminal fluoroolefins. In this process the fluoro vinyl stannanes substrates are prepared by the Horner-Wittig reaction of protected ketones with diethyl 1-fluoro-1-(phenylsulfonyl)methanephosphanate followed by conversion of the fluorovinyl sulfones to (fluorovinyl) stannanes by reaction with tributyltin hydride in refluxing benzene. Electrophilic fluorination of the vinyl stannanes is effected by reaction with 1-chloromethyl-4-fluoro-1,4-diazoniabicyclo[2.2.2.]octane bis(tetrafluoroborate).

Fuqua, S. A., et. Al, *Synthesis of 1,1-Difluoro Olefins. II. Reaction of Ketones With Tributylphosphine and Sodium Chlorodifluoracetate*, J. Am. Chem. Soc. 1965, 2543 disclose the formation of 1,1-difluoroolefins by reaction of aldehydes with triphenylphosphine and sodium chlorodifluoroacetate. The same reaction substituting a ketone for the aldehyde was not successful. However, replacement of triphenylphosphine with tributylphosphine and combining with N-methylpyrrolidone gave good yields.

U.S. Pat. No. 4,997,855 discloses the use of vinyl fluorides such as 11-bromo-1,1-difluoro-1,11-dodecadiene, 1,1-difluoro-2-methyl-1-dodecene, 1,1-difluoro-1-tetradecene and 1,1,2-trifluoro-1-dodecene for controlling nematodes and insects. Example 1 shows the preparation of such vinyl fluorides, e.g., the reaction of 1-difluoro-1-tetradecene with tridecylic aldehydes, dibromodifluoromethane and dimethylacetamide. Zinc dust is added to generate a precipitate. On filtering the filtrate is further purified to generate the desired product.

U.S. Pat. Nos. 4,839,390 and 4,968,851 disclose methods for combating arthropods and nematodes by the application of a long-chain halogen olefin. The long chain halogen olefins are obtained by reacting a triphenylphosphonium salt with chlorodifluoromethane in the presence of a $C_{1-4}$ alkyllithium compound.

U.S. Pat. Nos. 6,605,747 and 2002/0120,168 disclose the preparation of 1.1-difluoromethyl substituted cyclohexane ethers for use as liquid crystal compositions via a difluorovinyl intermediate. The difluorovinyl intermediate is formed by the reaction of the corresponding cyclohexanones or aldehydes with $CF_2Br_2$ and tributylphosphine.

Legros, J. et al, *Trifluoromethylcyclohexane As A New Solvent? Limits Of Use*, Tetrahedron 58 (2002) pp 4067–4070) discuss the stability aspects of trifluoromethylcyclohexane as a solvent. In the body of the article the dehydrofluorination of the trifluoromethyl group was attempted without success. Specifically, base dehydrofluorination of trifluoromethylcyclohexane using t-butyl Li in the presence of tetramethylenediamine or using t-BuOK or n-BuLi in $Et_2O$ are reported as unsuccessful.

BRIEF SUMMARY OF THE INVENTION

This invention relates to a process for the preparation of 1,1-difluorovinyl cycloaliphatic compounds from the trifluoromethyl substituted cycloaliphatic substrate, e.g., trifluoromethylcyclohexane and derivatives thereof. This process utilizes a "sterically hindered super-base" system represented by the formula $M^{+-NRR-}$ where M is Na or K and M is bonded to the nitrogen atom of a secondary or tertiary aliphatic amine (R) bearing secondary or tertiary aliphatic alkyl groups for effecting dehydrofluorination of the trifluoromethyl group leading to the 1,1-difluorovinyl based cycloaliphatic compounds. The sterically hindered super base can be formed by the, in situ, reaction of a sodium or potassium alkoxide, e.g., KtBuO with a lithium dialkylamide where the lithium is bonded to the nitrogen atom of an aliphatic amine bearing secondary or tertiary alkyl and cycloalkyl groups.

Significant advantages can be obtained by the use of this procedure and these include:

an ability to produce 1,1-difluorovinyl cycloaliphatic compounds in high yield;

an ability to produce 1,1-difluorovinyl cycloaliphatic compounds without the use of ozone-depleting chemicals, e.g., difluorodibromomethane or chlorodifluoromethane; and, an ability to generate 1,1-difluorovinylcyclohexane in high yields (>90%).

DETAILED DESCRIPTION OF THE INVENTION

The substrates employed in the reaction are trifluoromethyl substituted cycloaliphatic compounds and these compounds are converted to the 1,1-dilfluorvinyl cycloaliphatic compounds via the route shown:

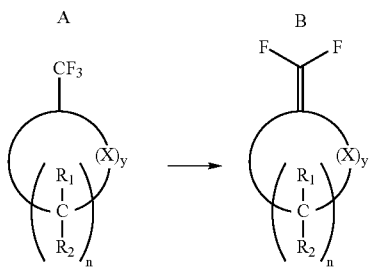

wherein $R_1$ and $R_2$ are H, $C_{1-20}$ alkyl, preferably $C_{1-3}$ alkyl, $C_{1-10}$ alkoxy and carboalkoxy, $C_{1-10}$ alkyl ether, $C_{2-10}$ alkenyl, aryl, $C_{1-6}$ alkyl substituted aryl, cycloaliphatic and fused polycyclic derivatives thereof;

n is an integer of at least 2, typically an integer from 4–10, and preferably, 5–8;

X is CH=CH, and y is 0 or 1,

Representative derivatives pendent from the cycloaliphatic ring as $R_1$ and $R_2$ groups include $OCH_3$, $CH_2OCH_3$, $COOCH_3$, $COOCH_2CH_3$, $SCH_3$, $CH_2S$—$CH_2$, $N(CH_3)_2$, $CH_2N(CH_3)CH_2$ etc. Specific alkyl groups are based upon $C_1$ to $C_{20}$ alkyl substituents, e.g., methyl, ethyl, propyl, isobutyl, pentyl, hexyl, heptyl, octyl, decyl, and dodecyl, cyclic aliphatic functionality such as cyclohexyl, and $C_{1-10}$ alkyl and alkoxy substituted cyclohexyl derivatives.

Examples of trifluoromethyl cycloaliphatic substrates which lead to difluorovinyl products include trifluoromethylcyclohexane, trifluoromethylcyclopentane, 1-trifluoromethyl-dihydronaphthalene, 4(4'-propylcyclohexyl)-1-trifluoromethylcyclohexane; 4-carboethoxy-1-trifluoromethylcyclohexane; 1-carboalkoxy-4 trifluoromethylcyclohexane; 3,3'-dimethyldioxane-1-trifluoromethylcyclohexane; 1-trifluoromethyl-dihydroanthracene and cycloaliphatic ring compounds bearing a $CF_3$ group of ring size $C_4$–$C_{10}$.

Surprisingly, the normally inherently stable trifluoromethyl cycloaliphatic compounds can be dehydrofluorinated by the sterically hindered super base described herein. Yet, it is also surprising that the trifluoromethyl substituted linear alkanes normally susceptible to dehydrofluorination do not respond to such sterically hindered base dehydrofluorination.

It has been found that a "sterically hindered super base" generated, in situ, can be employed to effect dehydrofluorination of the trifluoromethyl group to yield the 1,1-difluorovinyl cycloaliphatic compounds. The key components leading to the "sterically hindered super base" are sodium or potassium $C_{1-10}$ alkoxides and a lithium dialkylamide In the reaction medium it appears that an exchange occurs between the sodium or potassium with the lithium thereby forming a base expressed by the formula $M^+NRR^-$ where $M^+$ is sodium or potassium. It is important that the lithium dialkylamide is one in which the lithium ion is bonded to the nitrogen atom of an amine bearing secondary or tertiary alkyl or cycloalkyl groups.

Examples of sodium or potassium alkoxides suited for forming the sterically hindered base include sodium methoxide, potassium methoxide, sodium ethoxide, potassium ethoxide, sodium propoxide, potassium propoxide, potassium butoxide, and sodium butoxide. Potassium t-butoxide is the preferred alkali metal alkoxide used in forming the super base.

The other component of the "super base" is a lithium dialkylamide represented by the formula $Li^+ NRR^-$ where the R groups are secondary or tertiary alkyl groups of an amine, e.g., $C_{3-10}$ alkyl preferably 2° alkyl. Examples of lithium dialkylamides include lithium diisopropylamide, lithium dicyclohexylamide, lithium diisobutylamide, lithium 2,2-6,6-tetramethylpiperidide, lithium piperidide, lithium (N-methyl-N-t-butyl)amide, and lithium di-t-butyl amide.

The super base can be formed by adding from 1 to 5 moles sodium or potassium alkoxide per mole of lithium dialkylamide. To drive the reaction toward the sterically hindered base, it is common to employ a stoichiometric excess, e.g. from 10 to 50%, of the sodium or potassium alkoxide in relation to the lithium dialkylamide in the reaction medium.

The sterically hindered super base is added to the reaction medium in an amount of from 1 to 5 moles per mole of trifluoromethylcycloaliphatic substrate. Levels greater than 5 moles do not afford better yields and lesser levels tend to increase reaction times or decrease yields or both.

The dehydrofluorination reaction can be carried out in a wide range of liquid mediums, e.g., the reaction can be carried out in the presence of the trifluoromethyl cycloaliphatic compound neat or it can be carried out in the presence of solvents. Representative solvents suited for carrying out the reaction include hydrocarbons, fluorocarbons, and ethers. Examples include tetrahydrofuran, or hydrocarbons such as hexane or combinations of both. Other solvents may include fluorocarbons, e.g., Freon 113. Solvent levels of from 10 to 100% by weight of the trifluoromethyl organic compound can be used. The key, as with most reactions, is that the solvent is not reactive with the sterically hindered base or other components of the reaction.

The dehydrofluorination of the trifluoromethyl compound is carried out at temperatures below the decomposition of the trifluoromethyl cycloaliphatic compound to the boiling point of solvent or trifluoromethyl cycloaliphatic compound. Preferably low temperatures from –80 to +50° C., and most preferably from about –75° C. to 0° C. are employed and the reaction carried out under liquid phase conditions. Reaction times are influenced by the reaction temperature but typically the reaction can be completed in 30 to 300 minutes.

The following examples are provided to illustrate various embodiments of the invention and are not intended to restrict the scope thereof.

EXAMPLE 1

Synthesis Of 1,1-Difluorovinylcyclohexane Using Lithium Dicyclohexylamide/KtBuO

A 100 mL 3-neck round bottom flask equipped with a $N_2$ inlet tube, rubber septum and glass stopper was loaded with solid lithium dicyclohexylamide (0.86 g, 4.5 mmol). THF (3 mL), was added via a syringe and the mixture was cooled to –10° C. To this solution, a solution of trifluoromethylcyclohexane (456 mg, 3.0 mmol) in hexane (2 mL) was added drop-wise followed by addition of solid KtBuO (505 mg, 4.5 mmol). The mixture was stirred for 10 min. then brought to RT for 30 min. The reaction was monitored by GCMS for completion. After cooling again to –10° C., the reaction was quenched by addition of water (2 mL), extracted into hexane (10 mL); dried ($MgSO_4$), filtered and the solvent was distilled to obtain the product in 92% yield by GC.

The results show that the 1,1-difluorovinylcyclohexane was produced. (Mass spectrum: m/e 132 (M+). 19F NMR (CDCl$_3$) d −100 (2F). 1H NMR (CDCl$_3$) d 2.1 (4H, m), 1.5 (4H, m), 1.3 (2H, m).

EXAMPLE 2

Synthesis Of 1,1-Difluorovinylcyclohexane Using Lithium Diisopropylamide/KtBuO Using the apparatus described in Example 1, a solution of lithium diisopropylamide in THF/hexane was prepared from diisopropylamine (0.63 mL, 4.5 mmol) and 2.5M BuLi (1.8 mL, 4.5 mmol) at −50° C. The solution was brought to −10° C. and a hexane solution of trifluoromethylcyclohexane (456 mg, 3.0 mmol in 2 mL) was added followed by addition of KtBuO (505 mg, 4.5 mmol). The mixture was stirred for 10 min. then brought to RT for 30 min. The reaction was monitored by GCMS for completion. After cooling again to −10° C., the reaction was quenched by addition of water (2 mL), extracted into hexane (10 mL); dried (MgSO$_4$), filtered and the solvent was distilled to obtain the product in 97% yield by GC.

The results show that dehydrofluorination of the trifluoromethyl cyclohexane occurred using the described super base system.

EXAMPLE 3

Synthesis of 1,1-Difluorovinylcyclohexane Using Lithium 2,2-6,6- Tetramethylpiperidide/KtBuO Using the apparatus described above a solution of lithium 2,2-6,6-tetramethylpiperidide in THF/hexane was prepared from 2,2-6,6- tetramethylpiperidine (1.0 mL, 6.0 mmol) and 2.5M BuLi (2.4 mL, 6.0 mmol) at −50° C. The solution was brought to −10° C. and a hexane solution of trifluoromethylcyclohexane (456 mg, 3.0 mmol in 2 mL) was added, followed by addition of KtBuO (673 mg, 6.0 mmol). The mixture was stirred for 10 min. then brought to RT for 30 min. The reaction was monitored by GCMS for completion. After cooling again to −10° C., the reaction was quenched by addition of water (2 mL), extracted into hexane (10 mL); dried (MgSO$_4$), filtered and the solvent was distilled to obtain the product in 95% yield by GC.

The results show that the dehydrofluorination of the trifluoromethylcyclohexane was achieved using the described base.

EXAMPLE 4

Synthesis of 4(4'-propylcyclohexyl)-1-difluorovinyl-cyclohexane Using Lithium Diisopropylamide/KtBuO A solution of lithium diisopropylamide in THF/hexane was prepared from diisopropylamine (0.8 mL, 5.475 mmol) and 2.5M BuLi (2.2 mL, 5.475 mmol) at −50° C. The solution was brought to −10° C. and a hexane solution of 4(4'-propylcyclohexyl)-1-trifluoromethylcyclohexane (1.0 g, 3.65 mmol in 2 mL) was added followed by addition of KtBuO (0.614 mg, 5.475 mmol). The mixture was stirred for 10 min. then brought to RT for 30 min. The reaction was monitored by GCMS for completion. After cooling again to −10° C., the reaction was quenched by addition of water (2 mL), extracted into hexane (10 mL); dried (MgSO$_4$), filtered and the solvent was distilled to obtain the product in 98% yield by GC. The crude product in hexane was filtered through a plug of silica gel to obtain the pure compound, i.e., 4(4'-propylcyclohexyl)-1-difluorovinylcyclohexane.

Mass spectrum: m/e 256 (M+). 1H NMR (CDCl$_3$) d 2.40–2.50 (2H, m), 1.65–1.80 (8H, m), 1.25–1.40 (2H, m), 0.95–1.20 (8H, m), 0.80–0.90 (6H, m). 19F NMR (CDCl$_3$) d −100 (2F).

EXAMPLE 5

Synthesis of 4(4'-propylcyclohexyl)-1-difluorovinyl-cyclohexane Using Lithium Dicyclohexylamide/KtBuO A 100 mL 3-neck round bottom flask equipped with a N$_2$ inlet tube, rubber septum and glass stopper was loaded with solid lithium dicyclohexylamide (1.4 g, 7.3 mmol). THF (3 mL), was added via a syringe and the mixture was cooled to −10° C. To this solution, a solution of 4(4'-propylcyclohexyl)-1-trifluoromethylcyclohexane (1.0 g, 3.65 mmol) in hexane (2 mL) was added drop-wise followed by solid KtBuO (818 mg, 7.3 mmol). The mixture was stirred for 10 min. then brought to RT for 30 min. The reaction was monitored by GCMS for completion. After cooling again to −10° C., the reaction was quenched by addition of water (2 mL), extracted into hexane (10 mL); dried (MgSO$_4$), filtered and the solvent was distilled to obtain the product in 95% yield by GC.

EXAMPLE 6

Synthesis of 4(4'-propylcyclohexyl)-1-difluorovinyl-cyclohexane Using Lithium Tetramethylpiperidide/KtBuO Using the apparatus described above a solution of lithium 2,2-6,6-tetramethylpiperidide in THF/hexane was prepared from 2,2-6,6-tetramethylpiperidine (1.85 mL, 10.95 mmol) and 2.5M BuLi (4.38 mL, 10.95 mmol) at −50° C. The solution was brought to −10° C. and a hexane solution of the trifluoromethyl compound (1.0 g, 3.65 mmol in 2 mL) was added, followed by the addition of KtBuO (1.23 g, 10.95 mmol). The mixture was stirred for 10 min. then brought to RT for 30 min. The reaction was monitored by GCMS for completion. After cooling again to −10° C., the reaction was quenched by addition of water (2 mL), extracted into hexane (10 mL); dried (MgSO$_4$), filtered and the solvent was distilled to obtain the product in 48% yield by GC.

EXAMPLE 7

Reaction of 4(4'-propylcyclohexyl)-1-trifluoromethylcyclohexane Using Lithium Diethylamide/KtBuO In contrast to the previous examples, an amine having primary alkyl groups was used in place of an amine having secondary alkyl groups in the formation of the lithium dialkylamide. More specifically, a 100 mL 3-neck round bottom flask equipped with a N$_2$ inlet tube, rubber septum and glass stopper was loaded with solid lithium diethylamide (569 mg, 7.3 mmol). THF (3 mL), was added via a syringe and the mixture was cooled to −10°C. To this solution, a solution of 4(4'-propylcyclohexyl)-1 trifluoromethylcyclohexane (1.0 g, 3.65 mmol) in hexane (2 mL) was added drop-wise followed by addition of solid KtBuO (818 mg, 7.3 mmol). The mixture was stirred for 10 min. then brought to RT for 30 min. The reaction was monitored by GCMS for completion. After cooling again to −10° C., the reaction was quenched by addition of water (2 mL), extracted into hexane (10 mL); dried (MgSO$_4$), filtered and the solvent was distilled to obtain the —CF$_3$ hydrolysis product 4(4'-propylcyclohexyl)-1-N,N-diethylamidocyclohexane.

The desired product was not produced thus showing that the amine having primary alkyl groups was unsuited for forming the sterically hindered super base as in the previous examples and thereby effecting dehydrofluorination of the trifluoromethyl group. Mass spectrum: m/e 307 (M$^+$). 1H NMR (CDCl$_3$) d 3.2–3.5 (m, 4H), 1.7–1.9 (m, 12H), 0.8–1.5 (m, 21H).

EXAMPLE 8

Reaction of 4(4'-propylcyclohexyl)-1-trifluoromethylcyclohexane with KtBuO

In contrast to the previous examples it was attempted to effect dehydrofluorination of (4'-propylcyclohexyl)-1-trifluoromethylcyclohexane using the base potassium butoxide. More specifically, a solution of 4(4'-propylcyclohexyl)-1-trifluoromethylcyclohexane (1.0 g, 3.65 mmol) in hexane (2 mL) was added drop-wise to solid KtBuO (818 mg, 7.3 mmol). The mixture was stirred at RT. The reaction was monitored by GCMS for completion.

The results show only starting material was observed after 24 h.

EXAMPLE 9

Reaction of 4(4'-propylcyclohexyl)-1-trifluoromethylcyclohexane With Lithium Diisopropylamide In contrast to the previous examples, only a lithium dialkylamide was used with the nitrogen bonded to secondary carbon atoms. A solution of lithium diisopropylamide in THF/hexane was prepared from diisopropylamine (0.8 mL, 5.475 mmol) and 2.5M BuLi (2.2 mL, 5.475 mmol) at −50° C. The solution was brought to 10° C. and a hexane solution of 4(4'-propylcyclohexyl)-1-trifluoromethylcyclohexane (1.0 g, 3.65 mmol in 2 mL) was added. The mixture was stirred for 10 min. then brought to RT for 24 h. The reaction was monitored by GCMS for completion.

The results show only starting material was detected.

Summarizing the examples show the trifluoromethyl group pendent to a cycloaliphatic compound can be dehydrofluorinated to form 1,1 difluorovinyl cycloaliphatic compounds, particularly 1,1-difluorovinyl cyclohexanes and derivatives thereof, through the use of a sterically hindered super base formed by the, in situ, reaction of a sodium or potassium alkoxide with a lithium dialkylamide where the lithium is bonded to the nitrogen atom of a secondary or tertiary alkyl or cycloalkyl amine. Heretofore, the trifluoromethyl group pendent to a cycloaliphatic compound resisted dehydrofluorination even in the presence of strong bases. And, surprisingly the normally easy dehydrofluorination of trifluoromethyl substituted alkanes do not respond to dehydrofluorination with this base system.

What is claimed is:

1. A process for forming a 1,1-difluorovinyl cycloaliphatic compound which comprises: effecting dehydrofluorination of a trifluoromethyl cycloaliphatic compound where the trifluoromethyl group is pendent to the cycloaliphatic compound by reacting said trifluoromethyl cycloaliphatic compound with a sterically hindered base of the formula M$^+$NRR$^-$ where M is sodium or potassium and bonded to the nitrogen atom of an alkyl amine where the R groups are alkyl or cycloaliphatic having secondary or tertiary carbon atoms.

2. The process of claim 1 wherein the trifluoromethylcycloaliphatic compound is represented by the structure:

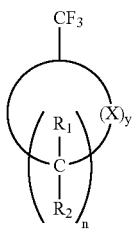

wherein R$_1$ and R$_2$ are H, C$_{1-20}$ alkyl, C$_{1-10}$ alkoxy, and C$_{1-10}$ carboalkoxy, C$_{1-10}$ alkyl ether, C$_{2-10}$ alkenyl aryl, alkyl substituted aryl, cycloaliphatic and fused polycyclic derivatives thereof; n is an integer of at least 2; X is CH=CH, and y is 0 or 1.

3. The process of claim 2 wherein n is 4–10.

4. The process of claim 3 wherein the sterically hindered super base is formed by the in situ reaction of a lithium dialkylamide of a secondary or tertiary alkyl or cycloalkyl amine and sodium or potassium alkoxide.

5. The process of claim 4 wherein the lithium dialkylamide is selected from the group consisting of lithium diisopropylamide, lithium dicyclohexylamide, lithium diisobutylamide, lithium 2,2-6,6- tetramethylpiperidide, lithium piperidide, lithium-N-methyl-N-t-butyl)amide, and lithium di-t-butyl amide.

6. The process of claim 5 wherein the sodium or potassium alkoxide is selected from the group consisting of sodium methoxide, potassium methoxide, sodium ethoxide, potassium ethoxide, sodium propoxide, potassium propoxide, potassium butoxide, and sodium butoxide, and potassium-t-butoxide.

7. The process of claim 6 wherein the sterically hindered super base is formed by the reaction of from 1 to 5 moles of sodium or potassium alkoxide per mole of lithium dialkylamide.

8. The process of claim 7 wherein the trifluoromethyl cycloaliphatic compound is selected from the group consisting of trifluoromethylcyclohexane, trifluoromethylcyclopentane, 1-trifluoromethyl-dihydronaphthalene, 4(4'-propylcyclohexyl)-1-trifluoromethylcyclohexane; 4-carboethoxy-1-trifluoromethylcyclohexane; 1-carboalkoxy-4 trifluoromethylcyclohexane; 3,3'-dimethyldioxane-1-trifluoromethylcyclohexane; 1-trifluoromethyl-dihydroanthracene and cycloaliphatic ring compounds bearing a CF$_3$ group of ring size C$_4$–C$_{10}$.

9. The process of claim 8 wherein from 1 to 5 moles sterically hindered super base are added per mole of trifluoromethyl cycloalphatic compound.

10. The process of claim 9 wherein y is 0 and n is 5–8.

11. The process of claim 10 wherein the alkoxide forming the super base is potassium-t-butoxide.

12. The process of claim 11 wherein R$_1$ and R$_2$ are H and n is 5.

13. The process of claim 7 wherein x is NR$_3$ and y is 1.

14. The process of claim 13 wherein R$_3$ is H, C$_{1-3}$ alkyl, C$_{1-3}$ alkoxy or C$_{1-3}$ carboalkoxy.

15. The process of claim 7 wherein X is 0 and y is 1.

16. The process of claim 15 wherein R$_1$ and R$_2$ are H.

17. The process of claim 9 wherein the trifluoromethyl cycloaliphatic compound is 4(4'-propylcyclohexyl)-1-trifluoromethylcyclohexane.

* * * * *